(12) United States Patent
Wimmer et al.

(10) Patent No.: US 11,478,128 B2
(45) Date of Patent: Oct. 25, 2022

(54) ENDOSCOPE WITH COVER AT DISTAL END OF CANNULA

(71) Applicant: Qioptiq Photonics GmbH & Co. KG, Göttingen (DE)

(72) Inventors: Christina Wimmer, Munich (DE); Martin Rothe, Munich (DE); Guido Zillmann, Moringen (DE)

(73) Assignee: Qioptiq Photonics GmbH & Co. KG

( * ) Notice: Subject to any disclaimer, the term of this patent is extended or adjusted under 35 U.S.C. 154(b) by 0 days.

(21) Appl. No.: 16/491,601

(22) PCT Filed: Mar. 7, 2018

(86) PCT No.: PCT/US2018/021250
§ 371 (c)(1),
(2) Date: Sep. 6, 2019

(87) PCT Pub. No.: WO2018/165229
PCT Pub. Date: Sep. 13, 2018

(65) Prior Publication Data
US 2020/0305692 A1 Oct. 1, 2020

Related U.S. Application Data

(60) Provisional application No. 62/467,908, filed on Mar. 7, 2017.

(51) Int. Cl.
*A61B 1/00* (2006.01)
*A61B 1/06* (2006.01)

(52) U.S. Cl.
CPC ...... *A61B 1/00096* (2013.01); *A61B 1/00137* (2013.01); *A61B 1/00142* (2013.01); *A61B 1/00167* (2013.01); *A61B 1/0676* (2013.01)

(58) Field of Classification Search
CPC ............ A61B 1/00096; A61B 1/00137; A61B 1/00142; A61B 1/00167; A61B 1/0676; G02B 27/0018; G02B 23/2423
(Continued)

(56) References Cited

U.S. PATENT DOCUMENTS 4,942,867 A * 7/1990 Takahashi .......... G02B 23/2423
600/176
5,951,464 A * 9/1999 Takahashi .......... A61B 1/00165
600/176
(Continued)

FOREIGN PATENT DOCUMENTS

JP H0233120 2/1990
JP H09-197292 A 7/1997
(Continued)

OTHER PUBLICATIONS

International Search Report and Written Opinion for PCT/US18/21250, dated Jun. 12, 2018.

*Primary Examiner* — Aaron B Fairchild
*Assistant Examiner* — Christen A. Sharpless
(74) *Attorney, Agent, or Firm* — Wolf, Greenfield & Sacks, P.C.

(57) ABSTRACT

An endoscope has a cannula, one and only one translucent or transparent cover at a distal end of the cannula, a light source and imaging system, both inside the cannula. The light source delivers light into the cover. At least some of that light passes through the cover to illuminate an inspection site inside the patient's body; some of that light is internally reflected at an outer surface of the cover to travel back toward an inner surface of the cover. The imaging system receives the light that has been reflected off the inspection site and returned to the endoscope through the cover. The components are configured such that none of the light that is internally reflected at the outer surface of the (Continued)

cover reaches an optical input of the imaging system directly (e.g., without being further reflected).

15 Claims, 7 Drawing Sheets

(58) Field of Classification Search
USPC .................................................. 600/175, 176
See application file for complete search history.

(56) References Cited

U.S. PATENT DOCUMENTS

| | | | |
|---|---|---|---|
| 6,328,691 B1* | 12/2001 | Rudischhauser | A61B 1/0008 600/133 |
| 6,503,196 B1* | 1/2003 | Kehr | A61B 1/00096 600/129 |
| 8,777,847 B2* | 7/2014 | Sato | A61B 1/0008 600/177 |
| 2003/0153813 A1 | 8/2003 | Kasel et al. | |
| 2012/0209074 A1 | 8/2012 | Titus | |

FOREIGN PATENT DOCUMENTS

| | | | | |
|---|---|---|---|---|
| JP | H09-265047 A | | 10/1997 | |
| JP | 2004-016455 A | | 1/2004 | |
| JP | 2004-041265 A | | 2/2004 | |
| JP | 2004-041458 A | | 2/2004 | |
| JP | 2004033587 A | * | 2/2004 | |
| JP | 2004208960 A | * | 7/2004 | |
| JP | 2014-66923 | | 4/2014 | |
| WO | 2014188147 | | 11/2014 | |
| WO | WO-2014188147 A1 | * | 11/2014 | ......... A61B 1/00096 |

* cited by examiner

ENDOSCOPE WITH COVER AT DISTAL END OF CANNULA

CROSS-REFERENCE TO RELATED APPLICATION(S)

This application is a 35 U.S.C. § 371 National Phase filing of International Application No. PCT/US2018/021250, filed on Mar. 7, 2018, entitled "ENDOSCOPE WITH COVER AT DISTAL END OF CANNULA," which claims priority and the benefit under 35 U.S.C. §119(e) to U.S. Provisional Patent Application No. 62/467,908, entitled, ENDOSCOPE WITH COVER FOR LIGHT DELIVERY COMPONENT (S), which was filed on Mar. 7, 2017. The disclosure of the prior application is incorporated by reference herein in its entirety.

FIELD OF THE INVENTION

This disclosure relates to an endoscope and, more particularly, relates to an endoscope that has a cover over a distal end of its cannula.

BACKGROUND

An endoscope is an instrument that can be introduced into the body to give a view of its internal parts.

It is generally desirable that an endoscope be as compact as possible, illuminate the inspection site (inside the patient's body) as fully as possible, be easy to care for, and be robust in design.

Typically, between uses, particularly when the uses will involve different patients, the endoscope will be sterilized.

Over time, exposure to multiple sterilization processes can degrade the endoscope's ability to perform in a highly effective manner.

SUMMARY OF THE INVENTION

In one aspect, an endoscope has a cannula, one and only one cover made from a translucent or transparent material at a distal end of the cannula, a light source and imaging system, both inside the cannula. The light source delivers light into the cover. At least some of that light passes through the cover to illuminate an inspection site inside the patient's body; some of that light is internally reflected at an outer surface of the cover to travel back toward an inner surface of the cover. The imaging system receives the light that has been reflected off the inspection site and returned to the endoscope through the cover. The components are configured such that none of the light that is internally reflected at the outer surface of the cover reaches an optical input of the imaging system directly (e.g., without being further reflected).

In a typical implementation, the geometry (e.g., relative configuration) of the cover, the light source, and the imaging system is solely responsible for ensuring that none of the light that is internally reflected at the outer surface of the cover reaches an optical input of the imaging system directly (e.g., without being further reflected). In those implementations, for example, the entirety of the cover, for example, is translucent or transparent; and no portion of the cover, through which the internally reflected ("first reflex") light travels, is made from a material that is not translucent or transparent. Thus, in a typical implementation, there are no portions of the cover, through which the ("first reflex") light passes, that block the transmission of the ("first reflex") light by virtue of not being translucent or transparent.

In some exemplary implementations, the cover has uniform, or at least substantially uniform, optical properties throughout. For example, in some implementations, the entire cover is made from the same translucent or transparent material throughout. Such covers may be formed as a "single piece" of the translucent or transparent material. The phrase "single piece," as used to describe the cover, should be construed to mean that the cover is a single continuous element (i.e., it does not have different parts or sections that can be readily separated from one another and put back together in a predictable manner and without effectively destroying the single piece of material).

In some implementations, the cover can be made from two or more pieces that are adhered or otherwise secured to one another. These multiple pieces can be made from the same material as one another, or can be different materials. Whether the same or different materials are used, it is the geometry (e.g., relative configuration) of the cover, the light source, and the imaging system that remains solely responsible for ensuring that none of the light that is internally reflected at the outer surface of the cover reaches an optical input of the imaging system directly (e.g., without being further reflected), and no portion of the cover, through which the internally reflected ("first reflex") light travels, is made from a material that is not translucent or transparent.

In implementations where the cover is made from more than one piece, if any other materials are present (e.g., adhesives or the like), then those materials are generally optical-grade materials and have optical properties that allow the resulting structure to behave identically to (or much like) a "single piece" of transparent or translucent material would behave.

In another aspect, an endoscope has a cannula, a single completely translucent or transparent cover that extends over a distal end of the cannula, a light source inside the cannula, and an imaging system inside the cannula. The cover has an outer first surface and an inner second surface. The light source delivers light to the distal end of the cannula. A first portion of that light passes through the cover to illuminate an inspection site inside the patient's body. A second portion of that light passes into the cover, but is internally reflected at the outer first surface back toward the inner second surface (i.e., back toward an interior of the cannula). The imaging system has an optical element inside the cannula that receives any light that has been reflected off the inspection site inside the patient's body and passed back through the cover. However, the cover, the light source, and the optical element are configured such that the second portion of the light (that passes into the cover but is internally reflected at the outer first surface back toward the inner second surface) does not reach the optical element directly (e.g., without having to be further reflected).

In yet one aspect, an endoscope includes a cannula for inserting into a patient's body, a light source inside the cannula configured to deliver light for illuminating an inspection site in the patient's body, and a translucent or transparent cover that extends over a distal end of the optical fiber bundle. The cover is coupled to the cannula in a manner that prevents fluids (e.g., liquids and/or gases) that are outside the endoscope from entering or reaching the light source, but that allows all of the light from the light source that exits a front, outer surface of the cover to reach and illuminate the inspection site, unobstructed.

In some implementations, none of the light that exits the front, outer surface of the cover hits or is blocked by any portion of the endoscope including the cannula. So if, for example, the endoscope is configured so that a cone of light (i.e., light delivered in a light cone pattern) is delivered through the front, outer surface of the cover, the entire light cone would be available to illuminate the inspection site (e.g., the parts of the body near the outside of the distal end of the endoscope). Generally speaking, a light cone can be considered a surface in space-time, represented as a cone in three dimensions, comprising all the points from which a light signal would reach from a particularly point simultaneously, and that therefore appear simultaneous to an observer at that point.

The phrase "inspection site" and the like, as used herein, refers generally to the space and objects around and near a distal end of the endoscope that can be illuminated, and potentially viewed, using the endoscope. However, the phrase "inspection site" generally excludes any part of the endoscope itself.

In some implementations, the light source may include a bundle of optical fibers or light guide(s) that are configured to deliver the light produced by a remote light generating device. Generally speaking, an optical fiber can be any kind of flexible, transparent fiber made, e.g., by drawing glass (silica) or plastic to a diameter usually slightly thicker than that of a human hair. Optical fibers may have a transparent core surrounded by a cladding material that also may be transparent, but that has a lower index of refraction. Light is kept in the core, and transmitted along the length of the fiber, by a phenomenon known as total internal reflection. In some implementations, the light source may include a light guide.

According to some implementations, there is an optical adhesive between a distal end of the light guide/optical fiber bundle and an inner surface of the cover. The optical adhesive can be virtually any kind of adhesive that is suitable for use in connection with the described application(s).

In some implementations, the cover is a translucent or transparent material (e.g., glass, silica, or the like). Such covers typically are disk-shaped, with an inner surface, an outer surface that is opposite the inner surface, and a cylindrical side surface that connects the inner surface and the outer surface. In a typical implementation, the outer surface is flat across its entirety. In some implementations, the inner surface is flat across its entirety too. In a typical implementation, the translucent or transparent material of the cover is substantially uniform (with substantially uniform translucence and/or transparency) throughout its entire volume (e.g., from every point on its outer surface, to every point on its inner surface, to every point along its cylindrical side surface, and every point therebetween).

In some implementations, the cover material is configured to define at least one cavity on its inner surface (e.g., that faces an interior of the endoscope). In those implementations, light source (e.g., the optical fiber bundle) typically extends into the cavity, and a distal end of the light source typically is adhered to a bottom surface of the cavity. In some implementations, there is no cavity in the material.

In some implementations, the cover has one or more thinner portions (e.g., at each cavity) and one or more thicker portions (elsewhere). In these implementations, the portion of the cover, through which light that has been reflected off the inspection site is returned to the endoscope for imaging, is generally thicker (quite a bit thicker, in fact), than a portion of the cover, through which the light from the light source passes when exiting the endoscope.

In a typical implementation, the endoscope/endoscopy system further includes an imaging system with optics (e.g., any kind of optical elements, like lenses, etc.) inside the cannula. In some of these implementations, the optics may be configured to receive light that has been reflected off the inspection site returned to the endoscope through the cover for imaging purposes. In those implementations, the light source may be generally configured to deliver light into the inspection site via a portion of the cover that forms a bottom of a cavity in the cover. Some of that light from the light source is internally reflected off an outer surface of the cover, causing the reflected light to travel back towards an inner surface of the cover. The light source, the cover (and its cavity), and the imaging system may be configured and arranged so as to ensure that none of the reflected light (off that first reflection) reaches an optical input of the imaging system directly off of that first reflection.

In some implementations, the endoscope's ability to prevent the reflected light from reaching the optical entrance to the imaging system directly off of the first reflection at the outer surface of the cover is a function of at least: an angle at which the light is delivered by the light source into the cover, a thickness of the cover (where the cavities are not), a thickness of a thin portion of the cover in front of the light source (e.g., at the cavity(ies)), and a distance between an optical exit of the light source and the optical entrance of the imaging system.

In some implementations, instead of being a single-piece of material, the cover may be made from two (or more) separate pieces that are held together (e.g., with an optical adhesive). In some of these implementations, the cover may include a first piece of translucent or transparent material that is uniform in thickness across its entire extent, a second piece of translucent or transparent material that is thicker than the first piece, yet still uniform in thickness across its entire extent, and an optical adhesive to secure the second piece to the first piece. The second piece can be substantially centered relative to the first piece and is smaller than and, therefore, covers only a portion of the first piece. In those implementations, the distal end of the light source can be adhered to a part of the first piece of translucent or transparent material that is not covered by the second piece of translucent or transparent material.

The cover typically is coupled to the cannula with a strong, fluid-tight connection (e.g., via soldering, or the like). Generally speaking, soldering refers to the use of a metal thin film coating in the solder area on the transparent cover and a solder material, e.g., AU and/or SN, that melts under heat and couples the cannula, which in some instances is a metal, to a thin film coating on the translucent cover, for example.

In some implementations, one or more of the following advantages are present.

For example, an endoscope may be provided that is particularly well suited to withstand multiple, even numerous, cycles of sterilization (using, e.g., low temperature gas plasma sterilization with hydrogen peroxide or the like). More particularly, the endoscope can be sterilized multiple, even numerous, times without degrading optical fiber performance as a result of the sterilization processes. This is because, as disclosed herein, the distal end of the endoscope, through which the optical fibers supply light, has a cover so that the optical fibers: 1) do not contact the patient's body during use, and 2) do not contact the plasma gas, hydrogen peroxide, and/or other sterilization-agents during sterilization.

In addition being able to withstand multiple, even numerous, cycles of sterilization (using, e.g., low temperature gas plasma sterilization with hydrogen peroxide or the like), in some implementations, the endoscope, in a typical implementation, is better able to withstand the environmental conditions associated with autoclaving, or the like than other types of flexible endoscopes. This is also due to the cover configuration disclosed herein.

Additionally, an endoscope may be provided that is particularly well suited to deliver a high degree of illumination to an inspection site (e.g., an area within the body of a patient). This is because the endoscope configuration, in a typical implementation, ensures that all of the light that exits the front surface of the endoscope ends up reaching and effectively illuminating the inspection site. More particularly, none of the light that exits the cover will hit (or be blocked by) any portion of the endoscope including, for example, its cannula.

A non-biocompatible material could be used for the fibers and their glue, since the fibers and the glue do not touch the patient. This could allow an improvement in the quality of the fibers themselves.

In some implementations, a light emitting diode (LED), if small enough, could also be used to supply light directly behind the cover glass. In those implementations, the output surface of the light emitting diode would be glued directly to a back surface of the cover. In those implementations, the LED could be provided instead of, or in addition to, the optical fibers. Moreover, if an LED were provided at the distal end of the endoscope (e.g., glued to the back surface of the cover), electrical conductors would be provided within the cannula up to the LED.

The cover of the fibers could be a very hard material, such as sapphire. In those implementations, this gives the advantage that scratching the surface of the fibers is very unlikely.

As used herein, the word "substantially," and similar words, should of course be construed according to their ordinary meanings. So, a "substantially flat surface," for example, is surface that is, for the most part (or entirely) flat, at least within expected manufacturing tolerances. Likewise, cavities that are identified as being "substantially identical" to one another are, for the most part (or entirely) identical, at least to the casual observer or within expected manufacturing tolerances. Similarly, "substantially centered" means for the most part (or entirely) centered at least within expected manufacturing tolerances.

Other features and advantages will be apparent from the description and drawings, and from the claims.

BRIEF DESCRIPTION OF THE DRAWINGS

Like reference numerals refer to like elements.

DETAILED DESCRIPTION

Figure 1:
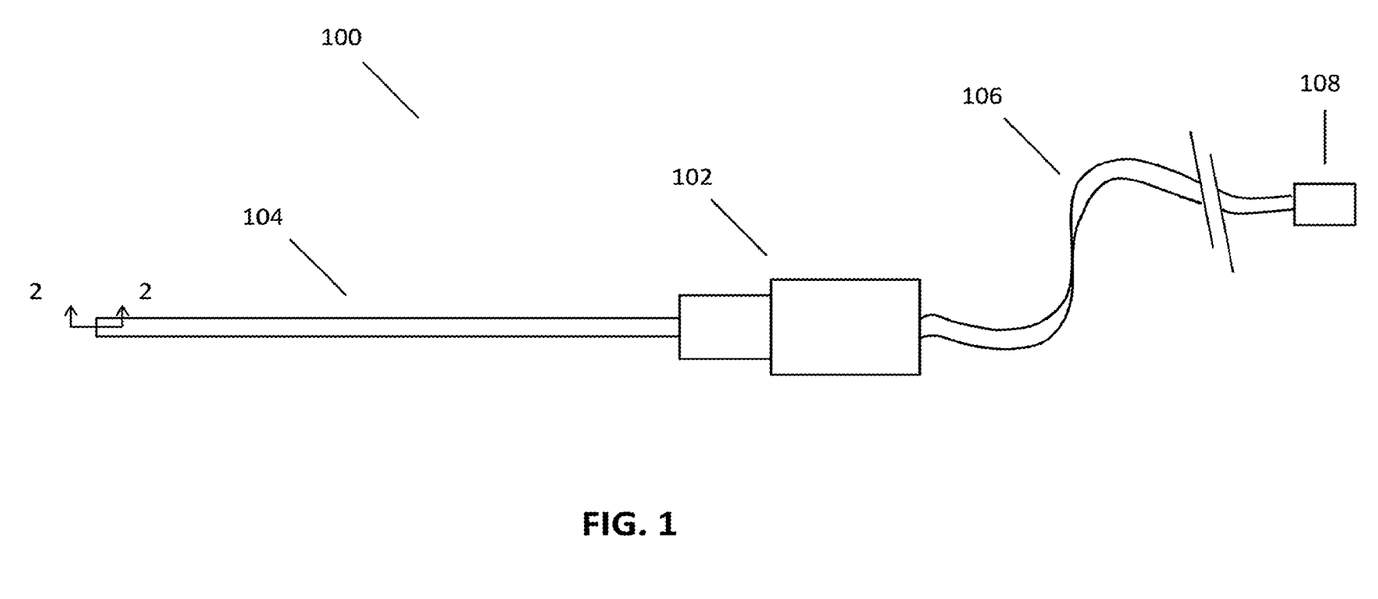
FIG. 1 is a schematic view of an exemplary endoscope.

FIG. 1 is a schematic view of an exemplary endoscope 100.

The endoscope 100 has an electronics housing 102, a cannula 104 that extends in a first direction from the electronics housing 102, a cable 106 that extends from the electronics housing 102, and a connector 108 at the end of the cable 106. During use, the connector 108, for example, can be connected to an external source of light and/or an electrical power source (to power a light) and/or to an external visual monitoring device (e.g., a video screen), none of which are shown in the illustrated figure.

The endoscope 100 is generally configured and operable to enable a doctor or other medical professional, for example, to perform endoscopy (i.e., visually examining an inspection site inside a patient's body). In this regard, during use, the cannula 104 of the endoscope 100 can be inserted, typically through a small opening in the patient's body, so that its distal end is proximate the inspection site inside the patient's body. Once inserted, the endoscope 100 can deliver light (e.g., via one or more optical fibers or light guides) through the cannula 104, and at least some of that light enters and illuminates the inspection site. The delivered light reflects off of body parts at the inspection site and reenters the distal end of the cannula 104, via the cover, to facilitate viewing or producing images of the inspection by the medical professional at an external viewing device (not shown in the illustrated figure, but which may be or include, for example, a video screen).

As disclosed herein, in detail, the endoscope 100 has a particular configuration of components at or near the distal end of the cannula 104 to ensure, among other things, very high quality imaging.

Figure 2:
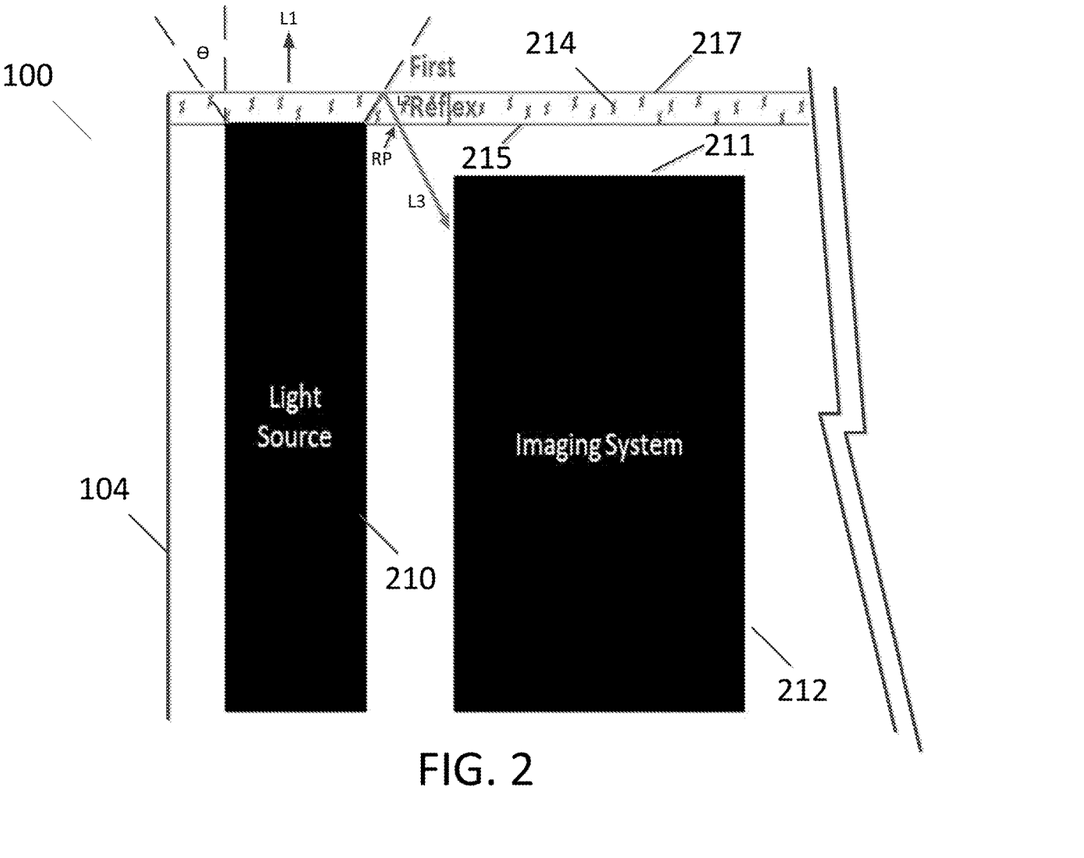
FIG. 2 is a partial, schematic, cross-sectional view (taken along 2-2 in FIG. 1) showing an exemplary configuration of components at the distal end of the cannula of the endoscope.

FIG. 2, for example, represents one exemplary configuration of components at the distal end of the cannula 104.

According to the illustrated implementation, the endoscope 100 has a single (i.e., one and only one), completely translucent or transparent, cover 214, that extends over (and may create a fluid or gas-tight seal over) an entire distal end of the cannula 104. A light source 210 and an imaging system 212 (with an optical element 211 that facilitates light entry into the imaging system 212) are inside the cannula at or near its distal end.

During operation, a portion of the light that is delivered by the light source 210 into the cover 214 is internally reflected at an outer surface 217 of the cover 214 to travel back toward an inner surface 215 of the cover 214. In the illustrated implementation, the light source 210, the cover 214, and the imaging system 212 are configured relative to one another such that none of the ("first reflex") light that is internally reflected at the outer surface 217 of the cover 214 and travels back toward the inner surface 215 of the cover 214 reaches an optical input (at 211) of the imaging system 212 directly (e.g., without being further reflected).

Moreover, in the illustrated implementation, the geometry (e.g., the relative physical configuration) of the cover 214, the light source 210, and the imaging system 212 is solely responsible for ensuring that none of the ("first reflex") light that is internally reflected at the outer surface 217 of the cover 214 reaches the optical input (at 211) of the imaging system 212 directly (e.g., without being further reflected). In the illustrated implementation, the entirety of the cover 214 is translucent or transparent; and no portion of the cover, through which the internally reflected ("first reflex") light travels, is made from a material that is not translucent or transparent.

In some exemplary implementations, the cover 214 has uniform, or at least substantially uniform, optical properties throughout. For example, in the illustrated implementation, the entire cover 214 is made from a single piece of translucent or transparent material throughout. The phrase "single piece," as used to describe the cover 214, should be construed as conveying the idea that the cover is a single continuous element (i.e., one that does not have different parts or sections that can be readily separated from one another and put back together in a predictable manner and without effectively destroying the "single piece" of material). The light source 210, which may include a bundle of optical fibers or a light guide for example, is configured to deliver light to the distal end of the cannula 104. In the illustrated implementation, the distal end of the light source 210 is in contact with (and may be adhered to) an inner surface of the cover 214. The distal end of the light source 210 need not be in contact with (or adhered to) the inner surface of the cover 214. However, having the distal end of the light source 210 in contact with the inner surface of the cover reduces optical losses. Moreover, adhering the distal end of the light source 210 to the inner surface of the cover 214 helps ensure and maintain good contact therebetween and proper alignment/positioning of the light source 210. Virtually any kind of optical grade adhesive can be used to adhere the distal end of the light source 210 to the inner surface of the cover 214.

A first portion L1 of the light that is delivered by the light source 210 to the distal end of the cannula 104 passes through the cover to illuminate the inspection site inside the patient's body. In a typical implementation, at least some of this light ends up being reflected back off of objects (e.g., the patient's body parts) in the inspection area, passes back through the cover 214, and enters the imaging system 212, via the optical element 211.

Essentially, the optical element 211 defines an aperture at a distal end of the imaging system, through which light must pass in order to enter the imaging system, and play any role in the image producing process in the imaging system 212. In other words, only light that passes through this optical element 211 participates in (or has any impact on) image production; any light that does not pass through the optical element 211 does not participate in (or have any impact on) the image production.

The optical element 211, which may be a lens or a transparent or translucent cover for the imaging system 212, is, in the illustrated implementation, near, but not in contact with, the cover 214. The distance between the distal surface of the optical element 211 and the inner surface of the cover 214 can have a variety of possible values, and may depend, at least in part, on the physical configuration of the light source 210 (and the light cone it produces), and the cover 214. In various implementations, this distance may be between, for example, 0.25 millimeters and 1 millimeter.

According to the illustrated configuration, the distance between the distal end of the imaging system 212 (optical element 211) and the outer surface 217 of the cover 214 is larger than the distance between the distal end of the light source 210 and the outer surface 217 of the cover 214.

The imaging system 212 produces images of the inspection site based on the light that enters the imaging system via the optical element 211 (e.g., the light that returns from the inspection site via the cover 214). Typically, any images (stills or videos) produced by the imaging system 212 are made available for viewing at a screen or lens, on the endoscope or to which the endoscope 100 is connected.

A second portion L2 of the light that is delivered by the light source 210 to the distal end of the cannula passes into the cover 214, but ends up being internally reflected at a front, distal, or outer surface 217 of the cover 214. This "first reflex" light L2 travels back through the cover 214, toward an inner surface 215 of the cannula 104. In a typical implementation, some portion L3 of this "first reflex" light L2 passes through the inner surface 215 of the cover 214 at a reentry point RP on the inner surface 215. The location of this reentry point RP on the inner surface of the cover 214 ensures that none of the reentry light L3 reaches, or can enter, the imaging system 212 (e.g., via the optical element 211). More particularly, the cover 214, the light source 210 (including the light cone LC produced by the light source), and the optical element 211 of the imaging system 212 are configured, in the illustrated implementation, such that none of that reentry light L3 reaches the imaging system 212 via the optical element 211 directly (e.g., without experiences at least two more internal reflections within the cover 214 first).

Thus, in a typical implementation, no portion of the "first reflex" light L2 enters the imaging system 212 (via the optical element 211) and, therefore, none of the "first reflex" light can interfere with image production. Therefore, the images of the inspection site produced by the endoscope can be free of such interferences. It is possible, of course, that some light (e.g., light that is internally reflected a second and third time inside the cover 214 may eventually reach the optical element 211 and enter the imaging system 212. However, after multiple internal reflections, any such internally reflected light that might enter the imaging system 212, via the optical element 211, would be minute, and any possible negative effects associated with that light entering the imaging system 212 would be largely negligible.

Thus, it can be seen that the relative geometry of the system components (i.e., the light source 210 (and its light cone LC), the imaging system 212/optical element 211, and the cover 214), produce the indicated, and advantageous result—i.e., that no portion of the "first reflex" light L2 (or reentry light L3) enters the imaging system 212 directly and, therefore, no portion of that "first reflex" light can interfere with image production by the endoscopy system. There are a variety of ways that this relative geometry can be configured.

Thus, in a typical implementation, the endoscope 100 can provide better, clearer images of an inspection site (e.g., inside a person's body).

In a typical implementation, the cover 214 also prevents bodily fluids and other foreign objects from entering the distal tip of the cannula 104, where they might otherwise cause problems and/or contamination. This is so especially in implementations where the cover 214 creates a seal against the distal end of the cannula 104. Other advantages are possible as well. For example, between uses, especially when sequential uses will involve different patients, the endoscope 100 must be sterilized. Sterilization can be achieved using any one of a variety of techniques including, for example, low temperature gas plasma sterilization with hydrogen peroxide (the likes of which may be implemented with a STERRAD® 100NX system), or exposure to high-pressure saturated steam in an autoclave. The endoscope 100 of FIG. 1 is well-suited to endure environmental conditions (e.g., high temperatures, and/or moisture) associated with these sterilization techniques, particularly, where a tight seal exists between the cover 214 and the cannula 104.

Moreover, in a typical implementation, the endoscope 100 is well suited to withstand multiple, even numerous, cycles of sterilization (using, e.g., low temperature gas plasma sterilization with hydrogen peroxide or the like). Typically, these multiple sterilizations, which may cause problems in other types of endoscopes, do not degrade optical performance of the endoscope 100 to a noticeable degree. This is particularly true in instances where the distal end of the endoscope is sealed by the cover, and where the cover is configured such that the optical fibers/light guides (and other internal components): 1) do not contact the patient's body during use, and 2) do not contact the plasma gas, hydrogen peroxide, and/or other sterilization-agents during sterilization.

Moreover, in some implementations, the cover is configured so that all of the light that passes through the front surface of the cover 214 reaches the inspection site, without being blocked by the sides of the cannula or other physical structure, for example, that might extend past the plane in which the outer surface of the cover 214 lies. In addition being able to withstand multiple, even numerous, cycles of sterilization (using, e.g., low temperature gas plasma sterilization with hydrogen peroxide or the like), in some implementations, the endoscope 100, with its cover configuration, may be better able to withstand the environmental conditions associated with autoclaving (including, e.g., exposure to high-pressure saturated steam at approximately 132° C. for approximately 15-20 minutes) than other types of flexible endoscopes.

Figure 3:
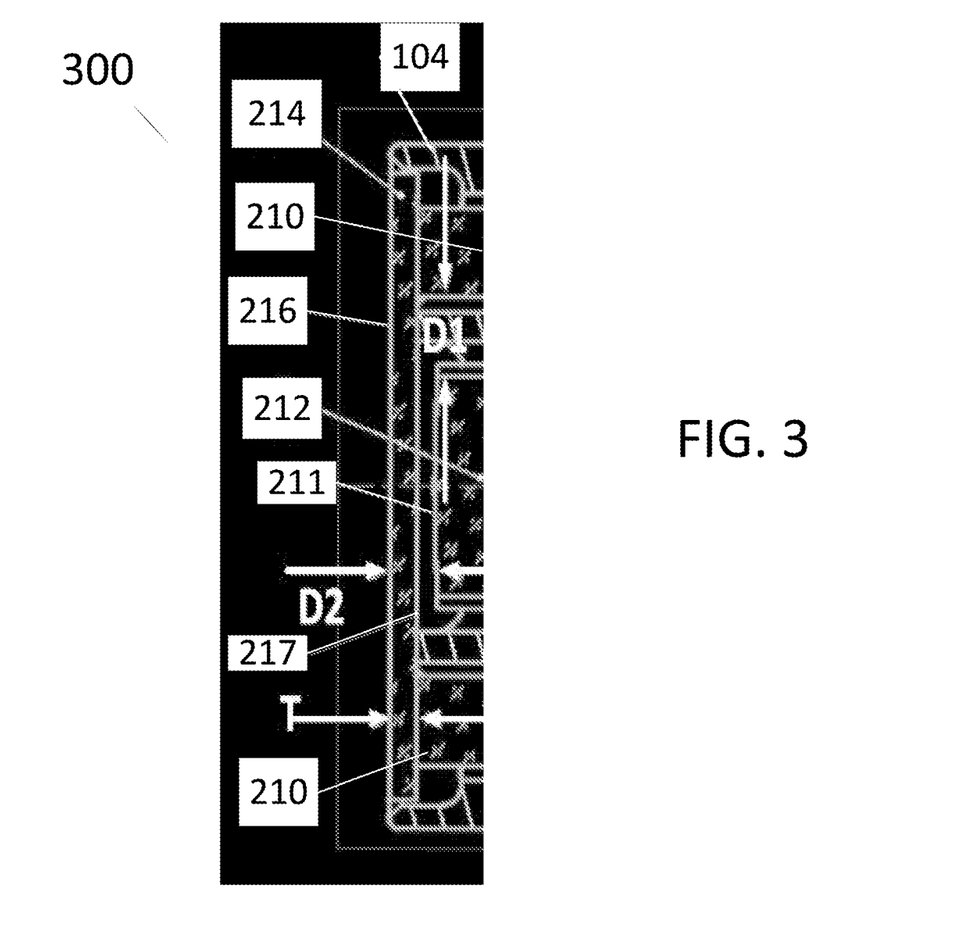
FIG. 3 is a partial, schematic, cross-sectional view (taken along 2-2 in FIG. 1) showing another, more detailed, exemplary configuration of components at the distal end of the cannula of the endoscope.

FIG. 3 is a partial, cross-sectional view showing an exemplary configuration of components at a distal end of an endoscope 300.

The endoscope 300 in FIG. 3 is similar in some ways to the endoscope 100 represented in FIG. 1. For example, the endoscope 300 in FIG. 3 has a cannula 104 for inserting into a patient's body. A translucent or transparent cover 214 extends over a distal end of the cannula 104. The cover 214 has a flat outer surface 216 and a flat inner surface 217 (opposite the outer surface). There is a light source 210 (two shown) inside the cannula 104. Each light source 210 is in direct physical contact with the cover 214, and is configured to deliver light into the cover 214, some of which passes through the cover 214 to illuminate an inspection site inside the patient's body. An imaging system 212 (with an optical component/imaging optics 211) is inside the cannula 104 as well. The imagining system 212 is configured to receive light (through its optical element 211, for example) that has been reflected off the inspection site in the patient's body and returned to the endoscope through the cover 214. The imaging system 212 uses that light to produce one or more images of the inspection site that can be viewed, for example, by a medical professional at a viewing station (e.g., a lens, video screen, or the like).

During operation, each light source 210 delivers light to the distal end of the cannula 104 and into the cover 214. A first portion of that light passes through the cover 214 to illuminate an inspection site inside the patient's body, and a second portion of the light passes into the cover 214 and is internally reflected at the outer surface of the cover 214 back toward the inner surface (without ever reaching the inspection site). The cover, the light source (and its light cone), and the optical element are configured such that no portion of the light that gets internally reflected at the outer surface of the cover 214 (without ever reaching the inspection site) reaches the optical element 211 or enters the imaging system 212, directly (e.g., without being further reflected inside the cover 214).

There are many different physical configurations and operational characteristics that can produce this result. In one exemplary implementation, each light source 210 produces a light cone that is 83 degrees, the cover 214 has a uniform thickness T of 0.3 millimeters, the distance D1 between each light source 210 and the imaging system 212 or optical element 211 is 0.73 millimeters, the distal front surface of the imaging system 212 is separated from the inner surface of the cover 214 (with empty space therebetween), the distance D2 between the distal front surface of the imaging system 212 and the outer surface of the cover 214 is 0.5 millimeters, and the distal end of each light source 210 is in physical contact with an inner surface of the cover 214.

These dimensions can, of course, vary without losing the advantage mentioned above—i.e., that the portion of the light that gets internally reflected at the outer surface of the cover 214 (without ever reaching the inspection site) does not reach the optical element 211 or enter the imaging system 212, directly (e.g., without being further reflected inside the cover 214). For example, in various implementations, the light cone can be between 75 and 91 degrees, the cover 214 thickness T can be between 0.1 and 0.4 millimeters, the distance D1 can be between 0.6 and 0.9 millimeters, and/or the distance D2 can be between 0.3 and 0.6 millimeters. In some implementations, the distal ends of the light sources 210 may be separated from (and not in direct contact with) the inner surface of the cover 214.

In some implementations, one or more of the foregoing dimensions can vary beyond what is specifically mentioned herein, while still producing the result that no portion of the light that gets internally reflected at the outer surface of the cover 214 (without ever reaching the inspection site) does not reach the optical element 211 or enter the imaging system 212, directly (e.g., without being further reflected inside the cover 214).

The illustrated endoscope has a rigid internal structure 328 that may contact and/or support the light sources 210 and the cover glass. This rigid internal structure 328 can be made of, or include, any one of a variety of different materials or combinations of materials. In one exemplary implementation, the rigid internal structure 328 is a metal.

In the illustrated implementation, the rigid internal structure 328 extends to, and contacts, the cover 214. Moreover, in some implementations, there is an adhesive material between the cover 214 and the portion of the rigid internal structure 328 that contacts the cover 214.

In some implementations, the rigid internal structure 328 may surround, support, and/or guide the light source(s) 210 through the cannula 104 toward the distal end thereof.

The cover 214 in the illustrated implementation can be attached to the cannula 104 and/or other components in a variety of different ways. In one exemplary implementation, the cover 214 secured to the cannula 104 with a soldered connection, which may, in some instances, create a seal therebetween that prevents fluids from outside the endoscope from entering the endoscope 300 or reaching the light source(s) 210.

The cover 214 is configured relative to the light sources 210 and the cannula 104, for example, to ensure that all of the light from the light sources 210 (e.g., in a light cone of 83 degrees) that exits the outer surface of the cover 214 reaches and illuminates the inspection site. In other words, none of the light that exits the outer surface of the cover 214 is blocked by any portion of the endoscope 300 (including the cannula 104).

Figure 4:
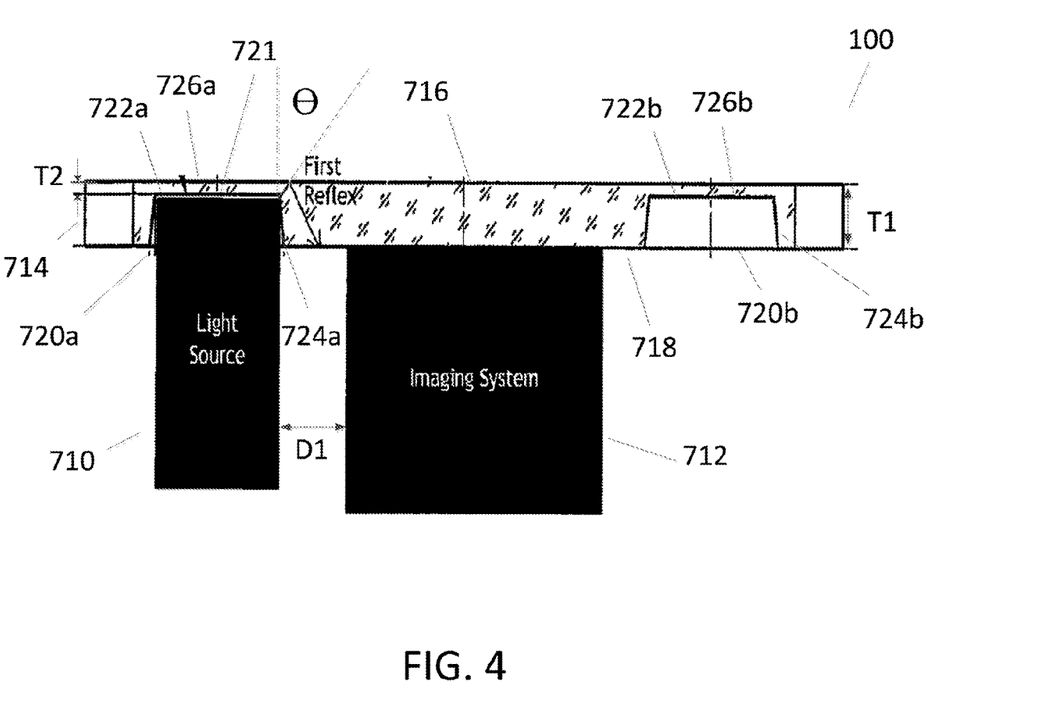
FIG. 4 is a partial, schematic, cross-sectional view (taken along 2-2 in FIG. 1) showing still another exemplary configuration of components at the distal end of the cannula of the endoscope.

FIG. 4 represents another exemplary configuration of components at the distal end of the cannula 104 in FIG. 1.

The illustrated figure shows a light source 710 (e.g., a bundle of optical fibers that can carry light) inside the cannula, an imaging system 712 (including, e.g., imaging optics) also inside the cannula, and a single-piece translucent or transparent cover 714 at a distal end of the cannula and that extends over and covers the light source 710 and the imaging system 712. The phrase "single piece" as used herein refers generally to the fact that the cover 714 in the illustrated implementation is made from one and only one piece of translucent or transparent material (e.g., glass or plastic) that cannot, for example, easily or predictably be separated into constituent parts and then put back together again.

The illustrated cover 714 has a first outer surface 716 that is substantially flat and faces an outward direction, and a second inner surface 718 that is opposite the first and that faces an inward direction. The figure shows that there are two cavities 720a, 720b in the second surface 718 of the cover 714. Of course, in various implementations, there can be virtually any number of cavities, from one and up, in the second surface 718 of the cover 714. Moreover, in a typical implementation, every cavity 720 in the second surface 718 of the cover 714 is substantially identical in shape and size. In the illustrated implementation, for example, cavity 720a is substantially identical (in size and shape) to cavity 720b. In one exemplary implementation, there are four cavities (symmetrically arranged across the second surface 718), each of which being substantially identical in size and shape to the others.

Each cavity 720a, 720b extends through part (in fact, most of), but not the entire thickness (T1) of the cover 714. For example, in various implementations, each cavity 720a, 720b can extend through at least 70%, or at least 80%, or at least 90% of the thickness (T1) of the cover 714. Each cavity 720a, 720b has a substantially flat bottom surface 722a, 722b and one or more sidewalls 724a, 724b that extend upward, with a slightly outward flare, from the flat bottom surface 722a, 722b, to define a slightly frustoconical (yet close to cylindrical) space therein. Each cavity 720a, 720b is generally configured so that a corresponding one of the light sources (e.g., a bundle of optical fibers 710) can fit into that slightly frustoconical (yet close to cylindrical) space such that the distal ends of the optical fibers can reach, or nearly reach, and be adhered to the bottom surface 722a, 722b of the cavity 720a, 720b (e.g., with an optical adhesive 721 or the like).

Since the cavities 720a, 720b do not extend through the entire thickness (T1) of the cover 714, there is a thin piece of cover material (having a thickness T2) that extends across the bottom 726a, 726b of each cavity 720a, 720b. In a typical implementation, this thin piece of material may be as thin as practical without unduly comprising the structural integrity of either the thin piece of material or the overall cover 714. In typical implementation, each of these thin pieces of cover material has a uniform, or at least substantially uniform, thickness across the entirety of the bottom 726a, 726b of each cavity 720a, 720b.

In a typical implementation, aside from the illustrated cavities 720a, 720b (and any other cavities that may be formed in the second surface 718 of the cover 714 to accommodate distal ends of other light sources), the rest of the cover 714 has a substantially consistent thickness (T1), with a substantially smooth, flat outer surface 716 and a substantially smooth, flat inner surface, which is part of 718. More specifically, in a typical implementation, there are no cavities anywhere in the substantially smooth, flat outer surface 716 of the cover 714.

The light source 710 (e.g., a bundle of optical fibers) in the illustrated implementation extends through the cannula all the way up to the cover 714. In fact, the distal end of the light source 710 extends into cavity 720a such that the distal ends of the optical fibers of the light source 710 either contact (or are very close to) the inner surface of the cover 714 at the bottom 726a of the cavity 720a. In a typical implementation, such as the one shown in the figure, the distal ends of the optical fibers of light source 710 would be adhered to the inner surface of the bottom 726a of the cavity 720a, with an optical adhesive with a high enough temperature stability. In a typical implementation, there is a separate light source (like light source 710) for each one of the cavities in the cover 714. So, although this is not specifically shown in FIG. 4, in a typical implementation, there would be a separate light source (e.g., a separate bundle of optical fibers) for cavity 720b and that separate light source would be arranged and configured relative to cavity 720b in much the same, if not exactly the same, way that light source 710 is arranged relative to cavity 720a. Of course, in a typical implementation, the same idea would apply for any other cavities that may be formed in the cover 714. Each one typically would get its own separate light source (i.e., bundle of optical fibers). Notably, the light for each or all of the light sources can originate at the same (or different) remote light generators (e.g., light emitting diodes, lasers, etc.).

The imaging system 712 in the illustrated implementation extends up to and contacts (or is at least very close to) the cover 714. In a typical implementation, the distal end of the imaging system 712 (i.e., the part that is closest to or touching the cover 714) is a window, though which light from the inspection site, for example, can pass. In a typical implementation such as the one represented in FIG. 2, the portion of the cover 714 that is in direct physical contact with, or closest to, the imaging system 712 (e.g., a window of the imaging system) is cavity-free. That is, there are no cavities in any portion of surface 718 that covers the imaging system 712 (or the window of the imaging system 712); instead, the entire portion of the surface 718 of the cover 714 that covers the imaging system 712 is smooth and flat.

The imaging system 712, in the illustrated implementation, is generally configured so that light (e.g., being reflected back from the inspection site) enters the imaging system 712 through the surface that faces (and that may be in direct physical contact with) the cover 714.

The optical entrance to the imaging system 712 is separated from the optical output of the light source 710 by a distance D1. In some implementations, all (or at least some) of the light sources in the endoscope 100 will be arranged in a symmetrical fashion relative to the imaging system 712. In implementations where all of the light sources in the endoscope 100 are arranged in a symmetrical fashion relative to the imaging system 712, all of the optical entrance to the imaging system 712 will separated from the optical output of each light source by the same distance (e.g., D1).

The light source 710 in the illustrated implementation is configured to deliver light into the inspection site (i.e., the space beyond the cover 714, inside the patient's body) via the portion of the cover 714 that forms the bottom 726a of the cavity 720a. Much of the light delivered by the light source 710, which may be in the approximate form of a cone, passes through the bottom 726a of the cavity 720a to illuminate the inspection site, but some of the light may be internally reflected off the outer surface of the cover 714 without exiting the cover 714. This first internal reflection (represented by the bent arrow labeled "first reflex") causes the first-reflected light to travel back towards the inner surface 718 of the cover 714, where some of that light will pass through the inner surface 718 (into the cannula) and some of that light will, once again, be internally-reflected back toward the front surface of the cover 714.

The degree to which any of the light delivered by the light source will be internally reflected when it first reaches the outer surface of the cover 714 (i.e., the "first reflex") is generally a function of the cover material, the angle Θ at which light is delivered into the cover 714 and, to a lesser degree, the wavelengths included in the light. Generally speaking, the light will be reflected when it first reaches the outer surface of the cover 714 (i.e., the "first reflex") if the angle of incidence Θ is greater than a certain limiting angle, called the critical angle.

Generally speaking, the light source 710, the cover 714 (and its cavity 720a), and the imaging system 712 in the illustrated implementation are configured and arranged so as to ensure that none of the light from that first reflection (i.e., the "first reflex") is able to reach the optical input for the imaging system 712 on that first reflection. As shown in the schematic representation in FIG. 2, for example, the "first reflex" light clearly falls short of reaching the optical entrance (i.e., the surface of the imaging system 712 closest to or touching the cover 714. As such, the "first reflex" light will not interfere with or limit the capabilities of the imaging system or the endoscope to produce accurate, high resolution images of the inspection site at the system's external viewing device (not shown).

Moreover, in a typical implementation, the illustrated endoscope 100 achieves this outcome (i.e., ensuring that none of the "first reflex" light is able to reach the optical input for the imaging system 712 on the first reflection) in a relatively compact endoscope (i.e., an endoscope with a small outer diameter cannula). This is desirable, of course, because any increases in cannula diameter make the endoscope more difficult to use and work with. In some instances, in fact, preventing any "first reflex" light from reaching the optical input for the imaging system 712 on the first reflection can be achieved by utilizing a configuration such as the one represented in FIG. 2 without increasing the cannula diameter at all.

The endoscope's ability to prevent the "first reflex" light in FIG. 2 from reaching the optical entrance to the imaging system 712 may be considered to be a function of: the angle Θ at which light is delivered by the light source into the cover 714, the thickness (T1) of the cover 714 from its front surface 716 to the portion of its back surface 718 that contacts (or is closest to) the imaging system 712, the thickness (T2) of the thin portion of the cover 714 in front of the light source 710, and the distance D1 between the optical exit of the light source 710 and the optical entrance of the imaging system 712.

Additionally, the fact that the light source 710 is so close to the front, outer surface 716 of the cover 714 ensures that all of the light (e.g., the entirety of the light cone) that exits the front surface 716 of the cover 714 will reach and end up effectively illuminating the inspection site. More particularly, none of the light that exits the front, outer surface 716 will hit (or be blocked by) any portion of the endoscope 100 including, for example, its cannula 104.

Figure 5:
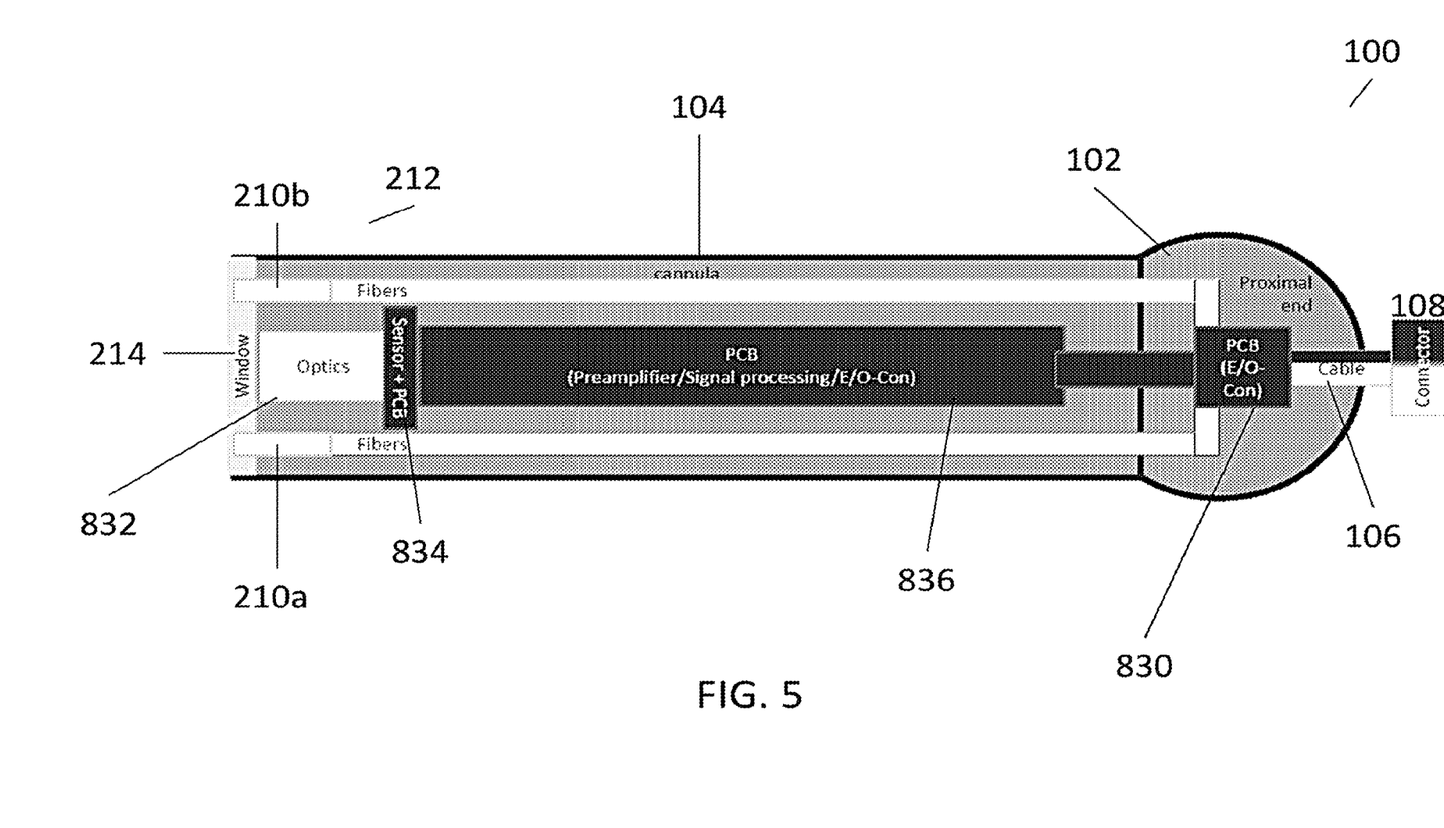
FIG. 5 is a schematic representation of an endoscope.

FIG. 5 is a schematic, cross-sectional view of an endoscope 100, like the one in FIG. 1, including an electronics housing 102, cannula 104, cable 106 and connector 108.

According to the illustrated implementation, the connector 108, which may be connected to an external light source (not shown), an external electrical power source (not shown), and/or an eternal viewing device (not shown), is at one end of the endoscope 100. The cable 106 extends from the connector 108 to the electronics housing 102. In a typical implementation, the cable 106 is configured to carry electricity and/or light between the connector 108 and the electronics housing 102.

Two bundles of optical fibers 210a, 210b (light sources) extend through the cannula 104 to the distal end of the endoscope 100. During use, light travels through the cannula 104 via the optical fiber bundles 210a, 210b and exits the endoscope 100, to illuminate the inspection site, through the cover 214 at the distal end thereof. As mentioned above, none of the light that exits the endoscope 100 through the cover 214 hits (or is blocked by) any portion of the endoscope 100 including, for example, the outer edges of its cannula 104.

The imaging system 212 in the illustrated implementation has optics 832 and an optical sensor and printed circuit board 834 (with electronics) associated with the optics 832. Light returns to the endoscope 100 from the inspection site through the cover 214 and enters the optics 832 which direct the light to optical sensors that convert the return light into electrical signals. Signals travel via electrical/or optical conductors and/or electronics on printed circuit boards 836 and 830 toward a proximal end of the endoscope.

Figure 6:
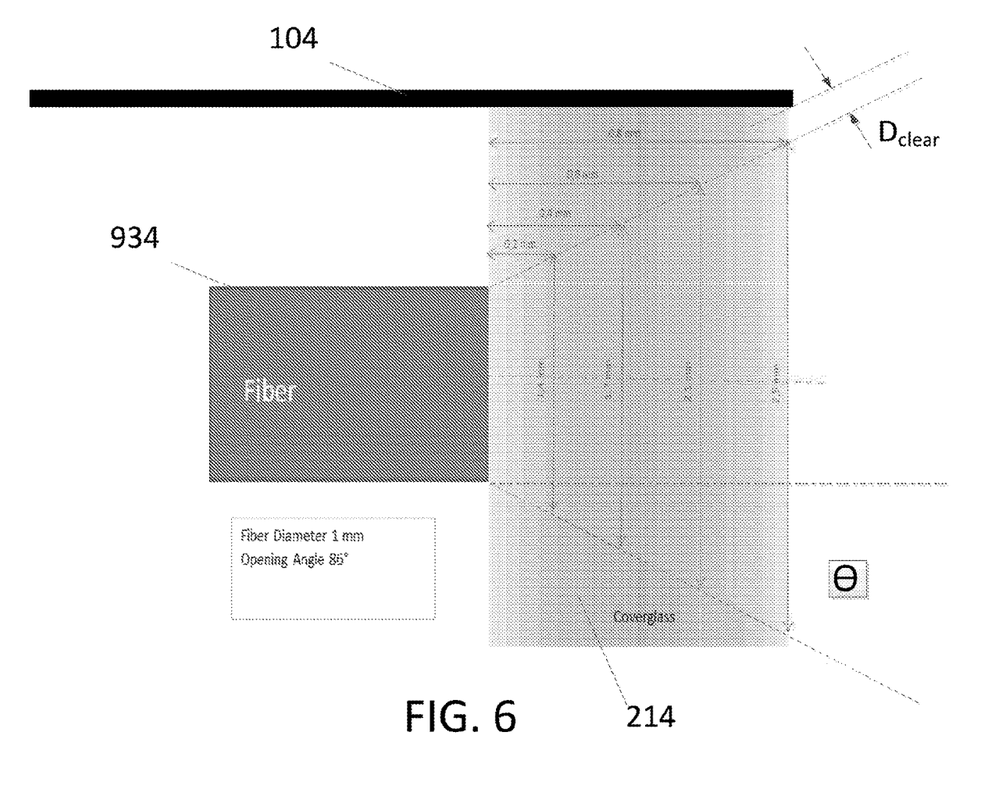
FIG. 6 is a schematic representation of a light cone being produced by a light source in an endoscope.

FIG. 6 is a schematic representation of a light cone being produced by an optical fiber 934, the likes of which may be part of one of the optical fiber bundles (light sources) in endoscope 100. The light is shown to be expanding as it passes through the cover 214. The fiber diameter in the illustrated implementation is 1 millimeter and the opening angle is approximately 86 degrees. As mentioned elsewhere herein, and shown in FIG. 6, in a typical implementation, the endoscope 100 is configured such that no part of the light cone will be obstructed by any part of the endoscope past the cover 214. More particularly, the upper edge of the light cone emitted by the optical fiber 934 clears the distal end of the cannula 104 by a distance ($D_{clear}$). $D_{clear}$, which can be virtually any dimension greater than zero. The endoscope 100, and the various components thereof, can have a variety of different dimensions. Generally speaking, compactness is considered to be highly desirable with endoscopes. As an example, the outer diameter of the cover 214 in an exemplary endoscope is approximately 8.3 millimeters. In another example, the outer diameter may be 8.5 millimeters. In yet another example, the outer diameter may be approximately 9 millimeters. This dimension, of course, can vary a bit, but practically speaking, the outer diameter is usually not more than 10 millimeters and usually not less than 8 millimeters. In fact, usually this dimension is mostly between 8 millimeters and 8.5 millimeters or between 8 millimeters and 9 millimeters.

The distal ends of each light source (i.e., the optical fiber bundles) in an exemplary endoscope are approximately 1.2 millimeters in diameter (of course, this is just an example). In some implementations, there are four separate light sources (e.g., circular fiber bundles). In such implementations, there would be four cavities in the back surface of the cover 214. In other implementations, there are two separate light sources (approximately half-moon shaped). In an alternative implementation, there could be just one bundle around the imaging system in a ring shape.

In some implementations, there are two optical entrances for the imaging system (a two camera system) and each optical entrance has a diameter of around 2.6 millimeters. But there could also be just one (or more than two).

The thickness of the cover 214 can vary, of course. In a typical implementation, however, the thicker portions of the cover are between 0.5 millimeters and 1 millimeter. However, in some implementations, the thicker portion could be as low as 0.3 millimeters.

The thinner portions of the cover 214 (e.g., where the cavities are formed) are typically between 0.1 millimeters and 0.05 millimeters. In some implementations, the thinner portions of the cover 214 could be as thick as 0.2 millimeters.

In a typical implementation, the distance between the optical exit of the light source and the optical entrance of the imaging system is 2 millimeters. However, in various implementations, this dimension can range, for example, between 1 and 4 millimeters.

Figure 7:
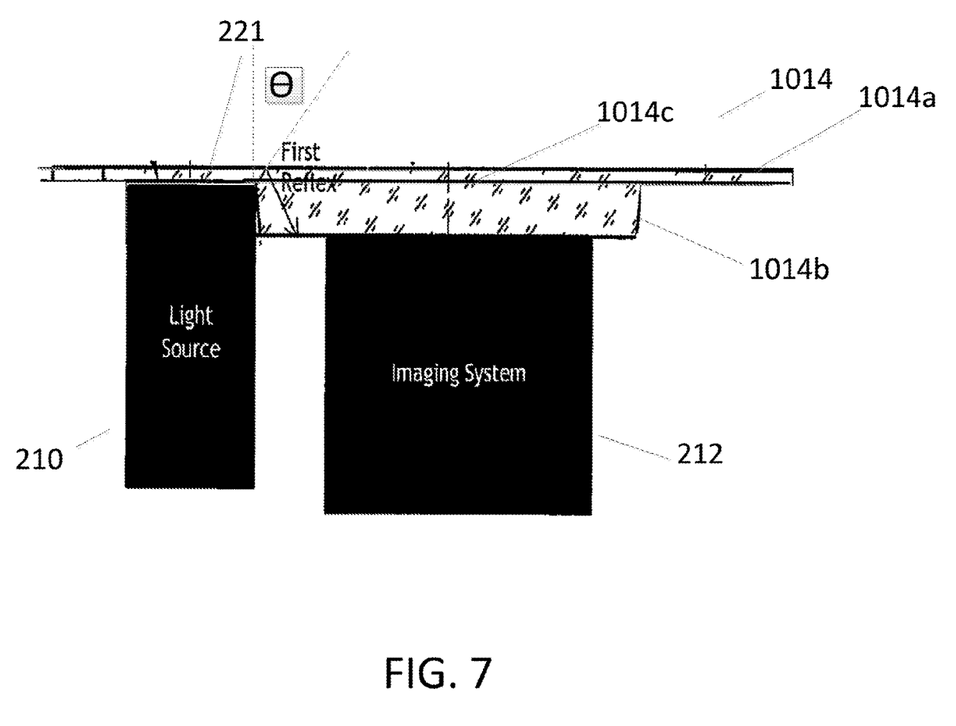
FIG. 7 is a partial, schematic, cross-sectional view (taken along 2-2 in FIG. 1) showing yet another exemplary configuration of components at the distal end of the cannula of the endoscope.

FIG. 7 is a partial, schematic, cross-sectional view (taken along 2-2 in FIG. 1) showing another exemplary configuration of components at the distal end of the cannula 104 of the endoscope 100.

The configuration represented in FIG. 7 is similar in many ways to the configuration represented in FIG. 4. For example, like the FIG. 4 configuration, the configuration represented in FIG. 7 has a light source 210, an imaging system 212, and a cover 1014. Moreover, like the FIG. 4 configuration, there is an optical adhesive 221 between the distal ends of the optical fibers in the light source 210 and the cover 1014.

Unlike the FIG. 4 configuration, however, the cover 1014 in FIG. 7 is not a single-piece cover; instead, the cover 1014 in FIG. 7 has two pieces 1014, 1014*b* that may be connected together with an optical adhesive 1014*c*. More particularly, in the illustrated implementation, the cover 1014 has a first piece 1014 that is thin, yet uniform in thickness, across its entire extent, and a second piece 1014*b* that is thicker than the first piece 1014, yet still uniform in thickness, across its entire extent. The optical adhesive 1014*c* keeps the second piece 1014*b* secured to the first piece 1014*a*. According to the illustrated implementation, the second piece 1014*b* is substantially centered relative to the first piece 1014*a* and covers only a portion of the first piece 1014*a*.

A number of embodiments of the invention have been described. Nevertheless, it will be understood that various modifications may be made without departing from the spirit and scope of the invention.

For example, the size (absolute and relative), shape and configuration of the endoscope and its various implementations can vary considerably. Additionally, other components and sub-components, not expressly disclosed herein, may be used with or added to the endoscope disclosed herein. Moreover, the disclosure herein can be adapted to various types of endoscope configurations including, for example, stereo endoscopes.

Additionally, the concepts including, for example, the covers disclosed herein may be adapted for use in connection with other applications that are not related to endoscopes.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

It should be understood that any relative terminology used herein is solely provided for the purposes of clarity in describing particular embodiments. It is not intended to limit the scope of what is described here to require particular positions or orientations. Accordingly, such relative terminology should not be construed to limit the scope of the present application.

Other implementations are within the scope of the claims.

What is claimed is:

1. An endoscope comprising:
   a cannula for inserting into a patient's body;
   one and only one cover consisting of a transparent or translucent material that extends over an entire distal end of the cannula, wherein the cover has an outer surface, and an inner surface opposite the outer surface;
   a light source inside the cannula configured to deliver light into the cover, at least some of which passes through the cover to illuminate an inspection site inside the patient's body; and
   an imaging system disposed inside the cannula configured to receive light that has been reflected off the inspection site in the patient's body and returned to the endoscope through the cover;
   wherein, during operation, a portion of the light that is delivered by the light source into the cover is internally reflected at the outer surface of the cover to travel back toward the inner surface of the cover;
   wherein an imaging system portion of the cover in front of the imaging system has a uniform first thickness that is thicker than a light source portion of the cover having a uniform second thickness in front of the light source; and
   wherein the light source, the cover, and the imaging system are configured relative to one another such that none of the light that is internally reflected at the outer surface of the cover and travels back toward the inner surface of the cover reaches an optical input of the imaging system directly, that is, without being further internally reflected; and
   wherein a) an angle at which the light is delivered by the light source into the cover, b) the first thickness, c) the second thickness, and d) a distance between an optical exit of the light source and an optical entrance of the imaging system are configured to prevent the light that is internally reflected at the outer surface of the cover and travels back toward the inner surface of the cover from reaching an optical input of the imaging system directly off of the internal reflection.

2. The endoscope of claim 1, wherein the relative configuration of the cover, the light source, and the imaging system is solely responsible for ensuring that none of the light that is internally reflected at the outer surface of the cover reaches an optical input of the imaging system directly.

3. The endoscope of claim 2, wherein no portion of the cover, through which the light that is internally reflected at the outer surface of the cover and travels back toward the inner surface of the cover travels, is made from a material that is not translucent or transparent.

4. The endoscope of claim 2, wherein the cover is formed as a single piece of a translucent or transparent material.

5. The endoscope of claim 2, wherein the cover is made from two or more pieces that are adhered or otherwise secured to one another.

6. The endoscope of claim 1, wherein the cover is coupled to the cannula in a manner that prevents fluids outside the endoscope from entering or reaching the light source, but allows all of the light from the light source that exits the outer surface of the cover to reach and illuminate the inspection site.

7. The endoscope of claim 6, further configured such that none of the light that exits the outer surface of the cover hits or is blocked by any portion of the endoscope, including the cannula.

8. The endoscope of claim 1, wherein the light source comprises a light guide or a bundle of optical fibers configured to deliver the light produced by a remote light generating device.

9. The endoscope of claim 8, further comprising:
an optical adhesive between a distal end of the light guide or the bundle of optical fibers and the inner surface of the cover.

10. The endoscope of claim 1, wherein the portion of the cover in front of the light source is configured to define at least one cavity that faces an interior of the endoscope.

11. The endoscope of claim 10, wherein the light source extends into the at least one cavity.

12. The endoscope of claim 11, wherein a distal end of the light source is adhered to a bottom surface of the at least one cavity.

13. The endoscope of claim 1, wherein the cover comprises:
a first piece of a translucent or transparent material that is uniform in thickness across its entire extent;
a second piece of the translucent or transparent material that is thicker than the first piece, yet still uniform in thickness across its entire extent; and
an optical adhesive to secure the second piece to the first piece,
wherein the second piece is substantially centered relative to the first piece and only partially covers the first piece.

14. The endoscope of claim 13, wherein a distal end of the light source is adhered to a part of the first piece of translucent or transparent material that is not covered by the second piece of translucent or transparent material.

15. The endoscope of claim 1, wherein the cover is coupled to the cannula via a soldered connection.

* * * * *